United States Patent [19]

Hazen et al.

[11] Patent Number: 5,326,703
[45] Date of Patent: Jul. 5, 1994

[54] METHOD OF DEGRADING POLLUTANTS IN SOIL

[75] Inventors: Terry C. Hazen, Augusta, Ga.; Geralyne Lopez-De-Victoria, Irmo, S.C.

[73] Assignee: The United States of America as represented by the United States Department of Energy, Washington, D.C.

[21] Appl. No.: 896,762

[22] Filed: Jun. 10, 1992

Related U.S. Application Data

[60] Continuation-in-part of Ser. No. 681,289, Apr. 8, 1991, abandoned, which is a division of Ser. No. 461,596, Jan. 5, 1990, abandoned.

[51] Int. Cl.$^5$ .......................... C12N 1/38; C12N 1/30; C12N 1/12
[52] U.S. Cl. ................... 435/262.5; 435/244; 435/250; 435/252.1; 435/821; 435/822
[58] Field of Search .............. 435/30, 244, 250, 262, 435/262.5, 264, 252.1, 821, 822

[56] References Cited

U.S. PATENT DOCUMENTS

| | | | |
|---|---|---|---|
| 4,859,594 | 8/1989 | Portier | 435/172.1 |
| 4,877,736 | 10/1989 | Fliermans | 435/183 |
| 5,024,949 | 6/1991 | Hegeman et al. | 435/262 |

OTHER PUBLICATIONS

Boyd, General Microbiology, 1984 pp. 169, 170.

*Primary Examiner*—David M. Naff
*Assistant Examiner*—Deborah K. Ware
*Attorney, Agent, or Firm*—Brian R. Tumm; Harold H. Dixon; William R. Moser

[57] ABSTRACT

A method and system for enhancing the motility of microorganisms by placing an effective amount of chlorinated hydrocarbons, preferably chlorinated alkenes, and most preferably trichloroethylene in spaced relation to the microbes so that the surprisingly strong, monomodal, chemotactic response of the chlorinated hydrocarbon on subsurface microbes can draw the microbes away from or towards and into a substance, as desired. In remediation of groundwater pollution, for example, TCE can be injected into the plume to increase the population of microbes at the plume whereby the plume can be more quickly degraded. A TCE-degrading microbe, such as *Welchia alkenophilia*, can be used to degrade the TCE following the degradation of the original pollutant.

8 Claims, 3 Drawing Sheets

Fig. 3.

```
INTRODUCE
TCE
TO PLUME
   ↓
MICROBES
MIGRATE
TO PLUME
   ↓
MICROBES
BIODEGRADE
PLUME
   ↓
INTRODUCE
WELCHIA
ALKENOPHILIA
   ↓
WELCHIA
ALKENOPHILIA
DEGRADE TCE
```

METHOD OF DEGRADING POLLUTANTS IN SOIL

The present invention relates to a method and system for enhancing the migration of microbes towards or away from a substance. The United States Government has rights in the present invention pursuant to Contract No. DE-AC09-76SR00001 between the U.S. Department of Energy and E.I. DuPont de Nemours & Co.

This is a continuation-in-part of copending application Ser. No. 681,289 filed on Apr. 8, 1991, which is a divisional application of application Ser. No. 461,596 filed Jan. 5, 1990, both now abandoned.

FIELD OF THE INVENTION

Discussion of Background

Use of microbes in industrial processes and pollution control continues to increase. Microbes are efficient and economical transformers of chemical compounds and intense effort is underway to find or engineer microbes suitable for various industrial purposes. The term microbes means motile bacterial, fungal, protozoan and metazoan species.

It was thought that certain types of compounds would not lend themselves to microbial degradation, compounds such as xenobiotic or synthetic chemicals, since these chemicals are usually toxic, do not occur naturally in the environment, and become recalcitrant when placed in a natural environment. However, research has shown that these, too, can be degraded. The range of applications for microbial degradation is thus greatly increased. In the treatment of effluents from sewage treatment plants and other industrial processes, microbial transformation of compounds is now common practice.

The major drawbacks in the utilization of microbes in remediation of contaminated groundwater and soils are the small size and sparse distribution of in situ microbial populations. Although found throughout the subsurface even to great depths, the concentration of microbes usually available for remediation of a plume of contaminants is generally low.

Various attempts have been made to enhance the population of microbes in the ground. Several of these are described in U.S. patents such as U.S. Pat. Nos. 4,765,902; 4,749,491; 4,576,717; 4,529,701; 4,447,541; 4,414,333; 4,401,569; 4,039,438; and 4,683,064. Generally, nutrients are injected or infused into the soil to promote the growth of the existing microbial colonies. Although fast reproducers, it takes time to build up a microbe population and not every microbe responds favorably to the same nutrient. Microbes may also be injected into a plume of contamination.

Microbes move in the ground sometimes randomly, sometimes with the flow of ground water and sometimes in response to taxis effects. A particular type of taxis is chemotaxis, defined as the movement of microorganisms toward or away from a chemical. Chemotaxis is positive or negative depending on whether it is toward or away from the chemical, respectively. Through chemotaxis, microbes seek optimum surroundings, such as those having nutrients, and avoid unfavorable ones, such as those without nutrients or with toxins.

In moving, microbes sometimes "run" and sometimes "twiddle". A run is a swimming motion in a gently curving path. A twiddle is a series of seemingly random movements followed by stationary "jiggling" in place. Chemotaxis is a bias in the motion in the direction of the chemical gradient.

Although chemotaxis is not well understood, it is believed that a set of proteins exist in the periplasm of the microorganisms, called chemoreceptors, and are specific for groups of closely-related compounds. A second set of proteins, methyl-accepting chemotaxis proteins (MCP), translates chemotactic signals to the flagellar motor. Methylation catalyzes the MCP to produce a chemical mediator that diffuses the flagellar motor so that it rotates in the same direction, thereby lengthening runs until the microorganism can no longer sense a gradient in the chemical substance. At some point the microorganism's receptors saturate and no further increase in the substance will increase the chemotactic response; in-fact, the normal chemotaxis response in deep subsurface bacteria is truly bimodal; that is, it changes from positive to negative after the critical concentration is achieved.

In industrial processes, microbes are moved mechanically or by slurrying them from one container to another. Mechanical action is sometimes disruptive. If the microbial action must be stopped, the microbes are sometimes destroyed in place with heat or chemical disinfectants.

SUMMARY OF THE INVENTION

It has been discovered that chlorinated hydrocarbons, preferably chlorinated alkenes and most preferably trichloroethylene, induce a surprisingly strong, positive, chemotactic response in a wide variety of naturally-occurring microbial species. Furthermore and also surprisingly, this response is monomodal, increasing as the concentration of chlorinated hydrocarbon increases. Accordingly, the present invention comprises a method and system for enhancing the motility of microbes by placing an effective amount of a chlorinated hydrocarbon in spaced relation to a substance so that the microbes are drawn to or away from the substance, as desired. The chlorinated hydrocarbon, preferably a chlorinated alkene, and most preferably trichloroethylene (TCE), may be placed in the substance to draw microbes to and through the substance to effect biodegradation of the substance. Alternatively, microbes in a substance can be drawn from the substance by placing the TCE away from the substance.

It is a feature of the present invention that this chemotactic response is very strong, approximately doubling the rate at which microbes move in soil for example. It is another feature of the present invention that the response is common to a wide variety of microbes that occur naturally. It is still another feature that the response is monomodal so that the response is positive for all concentrations.

An advantage of the present invention is that the chemotactic response of microbes can be used to induce an immigration or an emigration of large populations of microbes with respect to a substance, as desired, rather than wait for nutrients to enhance an existing microbial population or inject microbes into a system. If biodegradation of the substance is desired, for example, as with a plume of contamination, the insertion of TCE in the periphery of the plume will bring about a more rapid degradation of the contaminant.

Another advantage of the present invention is that microbes can be drawn from and kept from a substance where biodegradation is not desired.

Yet another advantage of the present invention is that microbes can be moved effectively by chemotaxis rather than mechanical means in a system where mechanical means is not desired if, for example, mechanical means may be too disruptive. These and other features and advantages inherent in the present invention will be apparent to those skilled in the various arts of microbial uses.

Reference is now made in detail to the present preferred embodiment of the invention, an example of which is given in the accompanying drawings.

BRIEF DESCRIPTION OF THE DRAWINGS

The accompanying drawings, which are incorporated in and form a part of the specification, illustrate the invention and, together with the description, serve to explain the principles of the invention. In the drawings:

FIG. 3 is a schematic diagram of an embodiment of the present invention as applied to pollution remediation.

DETAILED DESCRIPTION OF A PREFERRED EMBODIMENT

Figure 1:
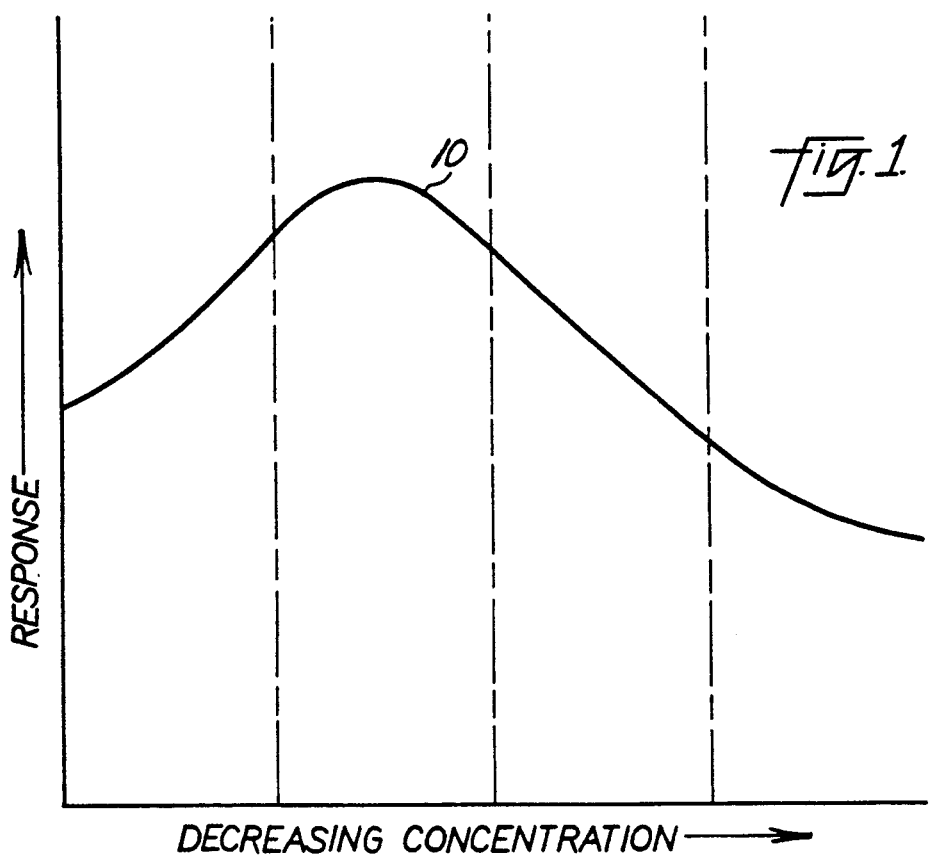
FIG. 1 is a graph showing the normal, bimodal chemotaxis response of microorganisms to nutrients.

It has been discovered that a wide variety of microorganisms, including most naturally occurring microorganisms, exhibit a surprising and extraordinary chemotaxis response to chlorinated hydrocarbons. The usual chemotaxis response, depicted in FIG. 1, is a positive response to nutrients, as might be expected, in which the microorganisms are attracted with increasing strength to higher concentrations of the nutrients. Beyond a critical concentration 10, however, the chemoreceptors appear to saturate and the response becomes negative.

Figure 2:
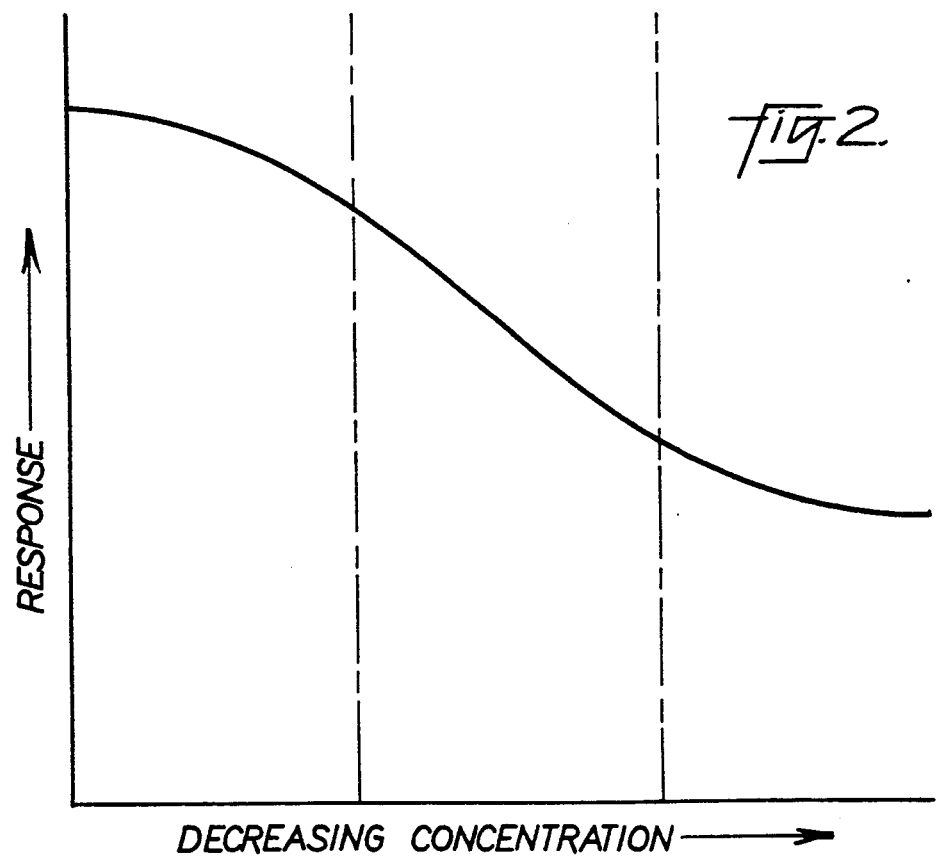
FIG. 2 is a graph showing the monomodal chemotaxis response of microorganisms to TCE.

In the case of chlorinated hydrocarbons, as illustrated by a graph of the response of microorganisms to TCE in FIG. 2, the response is greater and monomodal; that is, there is no critical concentration at which the chemoreceptors saturate. The response continues to increase with increasing concentration notwithstanding the fact that TCE and many other chlorinated hydrocarbons are toxic to these microorganisms.

The present invention is a method and system for enhancing the motility of microorganisms toward or away from a substance by placing an effective amount of chlorinated hydrocarbons in spaced relation to the microorganisms. If the migration of microorganisms away from the substance is desired, an effective amount of chlorinated hydrocarbons are placed at a distance from the substance so that the microorganisms are diverted from the substance or drawn out of the substance.

If the immigration of microorganisms into the substance is desired, the chlorinated hydrocarbons are placed on a side of the substance opposite that of the microorganisms, or, alternatively, in the substance.

In the instance of biodegradation of a substance, perhaps a contaminant, the chlorinated hydrocarbons may be placed just inside the periphery of the substance to enhance the assembling of a larger population of microorganisms at the periphery for biodegradation of the contaminant. When the contaminant at the periphery is degraded, chlorinated hydrocarbon-degrading microorganisms can be placed in the vicinity of the chlorinated hydrocarbons to degrade the chlorinated hydrocarbons and additional chlorinated hydrocarbons placed inside the new, smaller periphery of the remaining plume. As illustrated in FIG. 3, trichloroethylene (TCE) is introduced into a plume of contamination, causing subsurface microbes to migrate more quickly to the edge of the plume from the surrounding vacinity. The microbes degrade the plume in their enhanced movement to the TCE. The TCE is removed by introducing TCE-degrading microbes such as *Welchia Alkenophilia*.

The chlorinated hydrocarbons are preferably chlorinated alkenes and most preferably trichloroethylene (TCE).

The choice of the effective amount depends on the medium in which the microbes are found, the physical characteristics of the medium, the temperature of the medium, the presence of groundwater and any gradient in the groundwater in the medium, the presence of physical structures in the medium that might block the movement of the microorganisms, the nature and concentration of the substance, the extent of the substance, the presence of other taxis effects that compete or cooperate with the chlorinated hydrocarbons, the rate at which the migration is desired, the amount of migration desired, and the time available for assembling a population of microbes. Concentrations of at least $10^{-10}$ moles per liter produce a positive chemotaxis response; concentrations of at least $10^{-5}$ moles per liter are toxic to microorganisms.

The present invention can be seen in the following example.

EXAMPLE

Soil was mixed with diesel fuel and packed into sets of three sterile glass tubes. A reservoir of sterile mineral salts medium (MSM) was attached to one end of each tube of a set. In the first tube, the MSM contained no other additives; in the second, 100 ppb TCE was mixed with the MSM; and in the third, 100 ppb TCE was mixed with the MSM at one end and the opposing end was inoculated with a washed suspension of *Pseudomonas putida* containing the pWWO plasmid (a bacterium known to degrade petroleum hydrocarbons in soil). Each tube was prepared at the same time and incubated at 25° C. for several days. At the end of the incubation period, each tube was cut in half to form two sections and the contents of each section were analyzed for Total Petroleum Hydrocarbons (TPH). This experiment was repeated using a higher concentration of diesel fuel and a longer incubation time (22 days versus 12 for experiment 1). The results, in μg/g TPH with the number of samples shown in parentheses, are as follows:

|  | EXPERIMENT 1 | | EXPERIMENT 2 | |
| --- | --- | --- | --- | --- |
|  | SEC. 1* | SEC. 2 | SEC. 1 | SEC. 2 |
| MSM | 398.4 (8) | 384.6 (8) | 7353. (7) | 8492. (7) |
| MSM + TCE | 492.1 (1) | 517.9 (9) | 6779. (7) | 8848. (7) |
| MSM + TCE + bacteria | 390.9 (9) | 467.8 (9) | 6013. (9) | 7516. (9) |

*Section 1 is the section closer to the MSM reservoir

As will be evident from the results, in Experiment 1, using a lower diesel concentration, the MSM alone did not show significantly different concentrations from one part of the tube to the other. In the set with TCE added to the MSM but with only naturally occuring bacteria in the soil, the levels in the section of the tubes closer to the reservoir were much lower than in the other section, farther from the reservoir, indicating that the naturally occurring bacteria in the soil, chemotactically attracted by the TCE, had been degrading the diesel fuel.

The third set, with bioaugmentation using the *Pseudomonas putida*, shows an even greater degree of degradation in section 1 than in section 2. The naturally occurring bacteria, although including at least some bacteria capable of degrading diesel fuel, were augmented in their efforts by the *Pseudomonas putida*. Also, the *Pseudomonas putida* were drawn to the TCE, otherwise the difference in TPH between the sections would not have been so great.

In experiment 2, with higher diesel concentrations, the same trend was observed: lower concentrations in section 1 and higher in section 2 for both MSM plus TCE and the bioaugmented version. Probably because of the volatility of diesel fuel and the longer incubation time, the level in section 1 for MSM only is also relatively lower than in section 2.

These experiments confirm that TCE significantly lowers TPH by its effect on indigenous bacteria and shows an even greater effect in terms of biodegradation when naturally occurring bacteria are augmented with bacteria known to be degraders of the pollutant of interest.

The chemotactic effect of TCE is further illustrated by comparing it to that of dextrose, a known nutrient, and a substance that would be expected to draw bacteria to it. Table 1 shows the motility in centimeters per hour of nine bacterial samples for constant concentrations of TCE and dextrose. Table 2 shows the normalized chemotactic response of nine bacterial strains to various concentrations of dextrose. Table 3, again in relative units, shows the motility of the same microbes to TCE. The bacteria in the ninth columns of both Tables 2 and 3 are *Welchia alkenophilia*, as described in the Fliermans patent. A comparison of values at equal concentrations for the same bacteria will show the surprising chemotactic response of bacteria to TCE a bacterial toxin. The bacterium, *Welchia alkenophilia*, however, respond better to dextrose than TCE, notwithstanding the fact that *Welchia alkenophilia* is a known degrader of TCE. The foregoing experiments and tabular data illustrate the present invention in a quantitative way.

Figure 4:
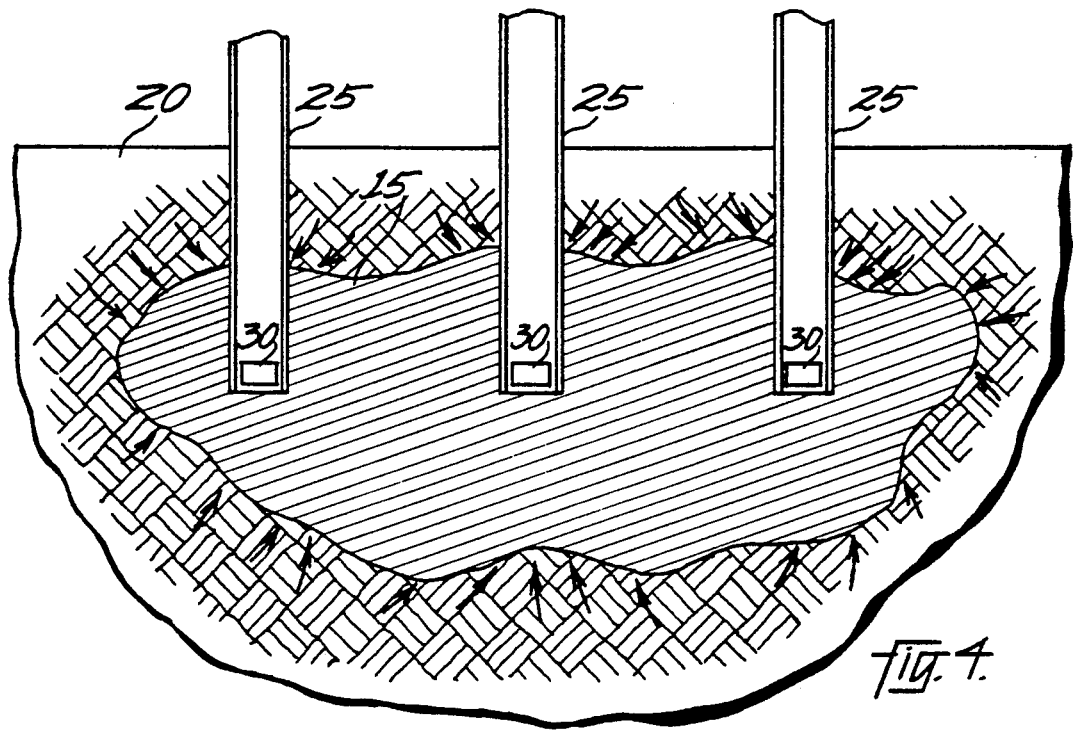
FIG. 4 is an illustration of an embodiment of the present invention as applied to remediate a plume of groundwater contamination at the start of the remediation of the contaminant.

As an example of an embodiment of the present invention, FIG. 4 shows a plume 15 of contamination in the ground. Into the plume is inserted a plurality of wells 25 for introducing by injection TCE 30 in an effective amount to induce the migration of microorganisms, as indicated by arrows in FIG. 4, naturally occurring in ground 20 to the periphery of plume 15. The microorganisms migrate to plume 15 where the degradation commences.

Figure 5:
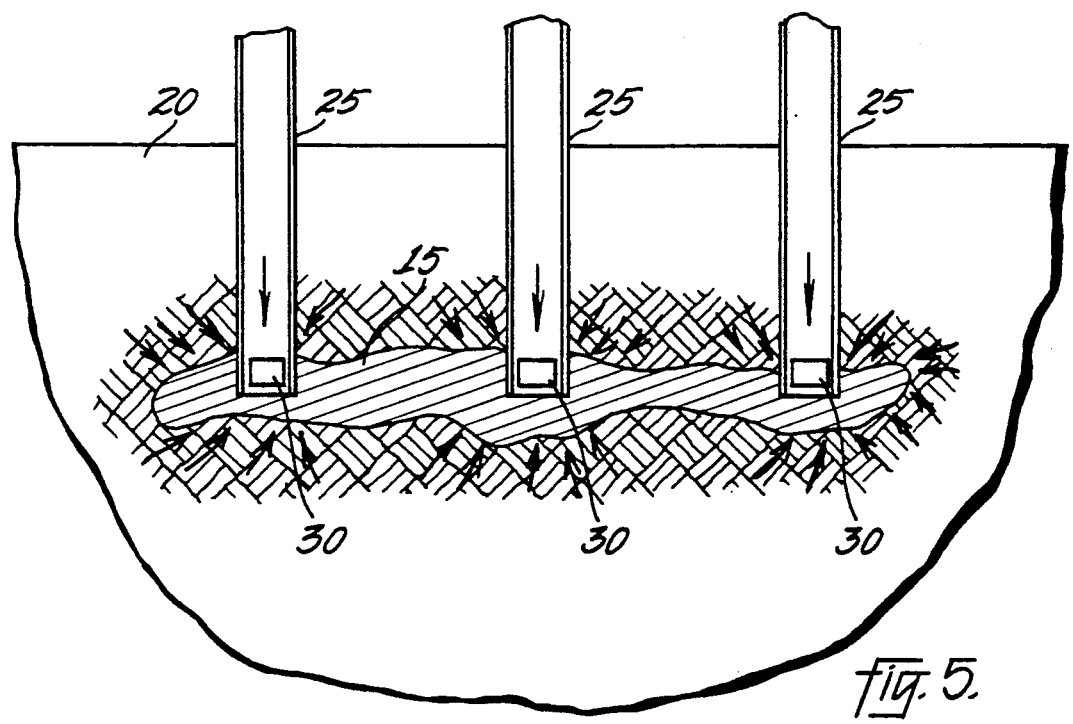
FIG. 5 is an illustration of an embodiment of the present invention as applied to remediate a plume of groundwater contamination at the end of the remediation of the contaminant and at the start of the removal of the TCE.

As shown in FIG. 5, when plume 15 has been reduced in size so that wells 25 are just within the boundary of plume 15, TCE-degrading microorganisms such as *Welchia alkenophilia* as described in a patent application having Ser. No. 07/256,429 filed on Oct. 12, 1988, now U.S. Pat. No. 4,877,736 are introduced in wells 25 to initiate the degradation of TCE.

Another example of the present invention is in the preservation of underground structures such as foundations or cabling from the effects of

TABLE 1

| BACTERIAL MOVEMENT IN SEDIMENT | | | | | | | | | |
| --- | --- | --- | --- | --- | --- | --- | --- | --- | --- |
| BACTERIA | AO231 | A0481 | B0388 | B0617 | B0703 | C0101 | C0397 | C0464 | CBF33 |
| DEXTROSE | 0.08 | 2.50 | 3.75 | 3.75 | 3.75 | 0.83 | 0.83 | 0.83 | 0.83 |
| TCE | 0.08 | 3.75 | 7.50 | 5.00 | 5.00 | 1.25 | 1.25 | 0.83 | 1.25 |

TABLE 2

| CHEMOTACTIC RESPONSE TO DEXTROSE | | | | | | | | | |
| --- | --- | --- | --- | --- | --- | --- | --- | --- | --- |
| BACTERIA | AO231 | A0481 | B0388 | B0617 | B0703 | C0101 | C0397 | C0464 | CBF33 |
| MOTIL | 1.00 | 1.01 | 1.11 | 0.96 | 1.09 | 1.10 | 1.02 | 1.00 | 1.06 |
| 1M | 1.43 | 1.39 | 2.08 | 0.81 | 1.75 | 0.88 | 2.06 | 0.98 | 0.32 |
| 10-1M | 1.35 | 0.64 | 1.61 | 0.83 | 1.13 | 1.33 | 2.05 | 1.30 | 1.07 |
| 10-2M | 1.56 | 1.02 | 1.52 | 1.20 | 1.43 | 1.53 | 1.55 | 0.65 | 1.49 |
| 10-3M | 1.63 | 0.97 | 2.63 | 1.34 | 1.30 | 1.58 | 1.86 | 0.86 | 1.76 |
| 10-4M | 1.86 | 0.83 | 2.42 | 1.05 | 0.76 | 1.25 | 2.12 | 0.73 | 2.09 |
| 10-5M | 1.88 | 1.15 | 2.46 | 0.73 | 0.58 | 1.23 | 1.37 | 0.75 | 1.79 |
| 10-6M | 2.17 | N/A | 2.69 | 1.41 | N/A | 1.28 | 1.41 | 1.25 | 1.12 |

TABLE 3

| CHEMOTACTIC RESPONSE TO TCE | | | | | | | | | |
| --- | --- | --- | --- | --- | --- | --- | --- | --- | --- |
| BACTERIA | AO231 | A0481 | B0388 | B0617 | B0703 | C0101 | C0397 | C0464 | CBF33 |
| MOTIL | 0.98 | 0.96 | 1.01 | 1.15 | 1.02 | 1.04 | 0.97 | 0.85 | 0.97 |
| 1M | N/A | N/A | 2.70 | 4.69 | N/A | 1.71 | N/A | 3.07 | 0.53 |
| 10-1M | N/A | N/A | 2.03 | 3.47 | N/A | 2.85 | N/A | 3.40 | 0.88 |
| 10-2M | 1.68 | 2.40 | 1.53 | 2.48 | 1.71 | 3.11 | 2.26 | 2.99 | 1.32 |
| 10-3M | 2.02 | 2.17 | 1.70 | 1.95 | 2.12 | 2.67 | 1.60 | 1.21 | 1.15 |

TABLE 3-continued

| BACTERIA | CHEMOTACTIC RESPONSE TO TCE | | | | | | | | |
|---|---|---|---|---|---|---|---|---|---|
| | AO231 | A0481 | B0388 | B0617 | B0703 | C0101 | C0397 | C0464 | CBF33 |
| 10-4M | 2.32 | 1.61 | 1.61 | 1.57 | 2.18 | 3.05 | 1.45 | 0.82 | 1.22 |
| 10-5M | 2.20 | 1.35 | 1.92 | 2.23 | 2.25 | 2.64 | 1.10 | 1.06 | 1.45 |
| 10-6M | 2.95 | 2.75 | 2.24 | 2.36 | 3.33 | 2.83 | 1.57 | 1.12 | 1.29 |
| 10-7M | 2.65 | 2.43 | 2.24 | 1.83 | 3.47 | 2.05 | 1.34 | 1.63 | 1.23 |
| 10-8M | 2.40 | 3.10 | 1.93 | 2.20 | 1.97 | 1.34 | 1.29 | 1.33 | 1.01 |
| 10-9M | 1.50 | 1.16 | 1.95 | 1.63 | 1.46 | 1.45 | 1.61 | 1.61 | 0.97 |
| 10-10M | 2.21 | 1.83 | 2.10 | 1.40 | 1.83 | 2.14 | 0.79 | 1.19 | 1.00 | microbial degradation. An effective amount of chlorinated hydrocarbon is placed in spaced relation to the structure, preferably on the inside of a microbial barrier external to the structure, and most preferably one which can easily receive a fresh charge of chlorinated hydrocarbon periodically, to draw the microbes in the ground to the chlorinated hydrocarbon and away from the structure. The chlorinated hydrocarbon, toxic to most microorganisms, additionally destroys them.

Another example of the present invention is a container for substances that are to be disposed of by shallow land burial and for which substances and container biodegradation is desired. The container can be treated with an effective amount of chlorinated hydrocarbons, preferably in selected locations in the container, to effect the more rapid degradation of its contents in those locations so as to give microbes access to the container interior.

Another example of the present invention is the use of enhanced chemotaxis in industrial processes to effect degradation of chemical substances for which mechanical movement of microbes is not desired, perhaps because it may be too disruptive. Alternatively, removal of microorganisms may be desired, perhaps to disinfect a substance or structure, where heat or other disinfectants are not desired or the removal of the organisms is preferred to their destruction in situ.

It will be evident to those skilled in microbial processes that there are many applications of the present invention where the enhanced motility of microorganisms is desired, where the control of the motility of microorganisms is desired, where the focusing of microorganisms is desired, all achievable according to the present method and system.

The foregoing description of the preferred embodiments of the present invention has been presented for purposes of illustration and description. It is not intended to be exhaustive or to limit the invention to the precise form disclosed, and obviously many modifications and variations are possible in light of the above teachings. The embodiments were chosen and described in order to best explain the principles of the invention and its practical application to thereby enable one skilled in the art to best utilize the invention in various embodiments and with various modifications as are suited to the particular use contemplated. It is intended that the scope of the invention may be defined by the claims appended hereto.

What is claimed is:

1. A method of degrading a concentration of a pollutant in soil, said pollutant concentration being above a preselected level, said soil containing naturally occurring bacteria, said method comprising the steps of:
   placing a quantity of tetrachloroethylene in said pollutant whereby said bacteria are drawn to said tetrachloroethylene and whereby said bacteria begin to degrade said pollutant;
   monitoring said pollutant concentration; and
   removing said tetrachloroethylene from said pollutant when said pollutant concentration has been reduced to said preselected level.

2. The method as recited in claim 1, wherein said tetrachloroethylene is removed by injecting a tetrachloroethylene-degrading bacteria into said tetrachloroethylene.

3. The method as recited in claim 1, wherein said tetrachloroethylene is removed by injecting *Welchia alkenophilia* into said tetrachloroethylene to degrade said tetrachloroethylene.

4. The method as recited in claim 1, wherein said quantity of tetrachloroethylene is between 1M and $10^{-10}$M.

5. The method as recited in claim 1, further comprising the step of injecting bacteria selected as known degraders of said pollutant near said pollutant.

6. A method of degrading a concentration of a pollutant in soil, said pollutant concentration being above a preselected level, said soil containing naturally occurring bacteria, said method comprising the steps of:
   placing a quantity of tetrachloroethylene in said pollutant so that said bacteria are chemotactically attracted to said tetrachloroethylene and whereby said bacteria begin to degrade said pollutant;
   monitoring said pollutant concentration; and
   inoculating said tetrachloroethylene in said pollutant with bacteria known to degrade tetrachloroethylene when said pollutant concentration has been reduced to said preselected level.

7. The method as recited in claim 6, wherein said bacteria known to be degraders of tetrachloroethylene include the species *Welchia alkenophilia*.

8. The method as recited in claim 6, wherein said quantity of tetrachloroethylene is between 1M and $10^{-10}$M.

* * * * *